United States Patent [19]

Rosen et al.

[11] Patent Number: 4,998,932
[45] Date of Patent: Mar. 12, 1991

[54] CATHETER WITH DISTALLY LOCATED INTEGRATED CIRCUIT RADIATION GENERATOR

[75] Inventors: Arye Rosen; Har'el Rosen, both of Cherry Hill, N.J.

[73] Assignee: AMT Inc., Wilmington, Del.

[21] Appl. No.: 346,873

[22] Filed: May 3, 1989

[51] Int. Cl.$^5$ ............................................. A61B 17/36
[52] U.S. Cl. ...................................................... 606/29
[58] Field of Search .................................. 128/395–398, 128/634, 664, 665; 606/13–15, 27–31

[56] References Cited

U.S. PATENT DOCUMENTS

| | | | |
|---|---|---|---|
| 4,643,186 | 2/1987 | Rosen et al. | 128/303.1 |
| 4,776,086 | 10/1988 | Kasevich | 128/784 |
| 4,860,744 | 8/1989 | Johnson et al. | 606/31 |
| 4,905,690 | 3/1990 | Ohshiro et al. | 128/385 |

OTHER PUBLICATIONS

"GaAs MMIC's Research Status in the U.S.A." by Ch'en, published by pp. 23-33 of the Proceedings of the 13th European Microwave Conference (1983).
"Optically Activated PIN Diode Switch Utilizing 2-D Laser Array at 808 nm as an Optical Source", published in the IEEE Transactions in Feb. of 1989.

*Primary Examiner*—Max Hindenburg

[57] ABSTRACT

A catheter includes at least two electrical conductors extending from the proximal to the distal ends. A semiconductor chip generator of electromagnetic radiation is located at the distal end and is energized by electrical power supplied by the electrical conductors. The chip may be a laser or include an oscillator for generating electromagnetic radiation at a selected frequency or frequencies. In one embodiment, two chip radiation generators are located distally, each connected to one of the conductors. A third conductor is connected in common to both chips, whereby they may be energized independently. An axial aperture may be provided for a guide wire. A balloon may surround the distal end of the catheter, and may be inflated by way of another axial aperture.

16 Claims, 4 Drawing Sheets

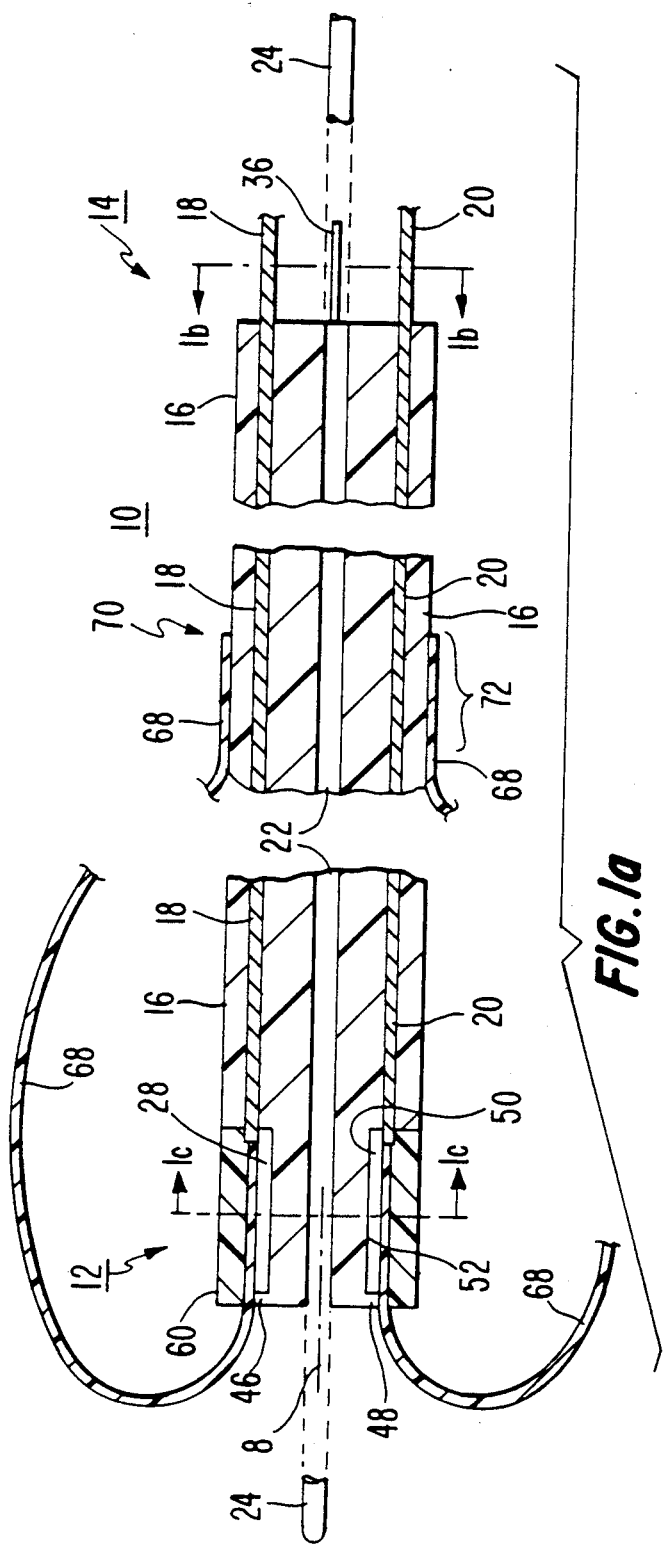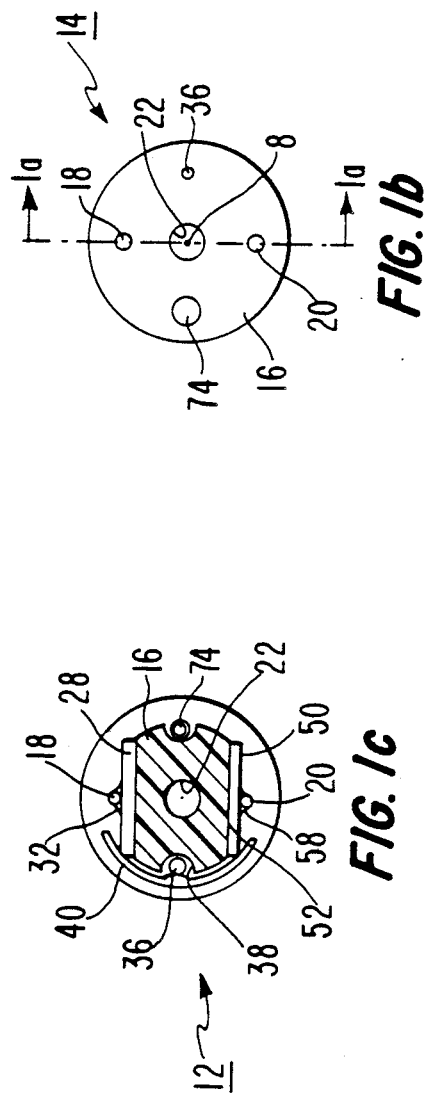

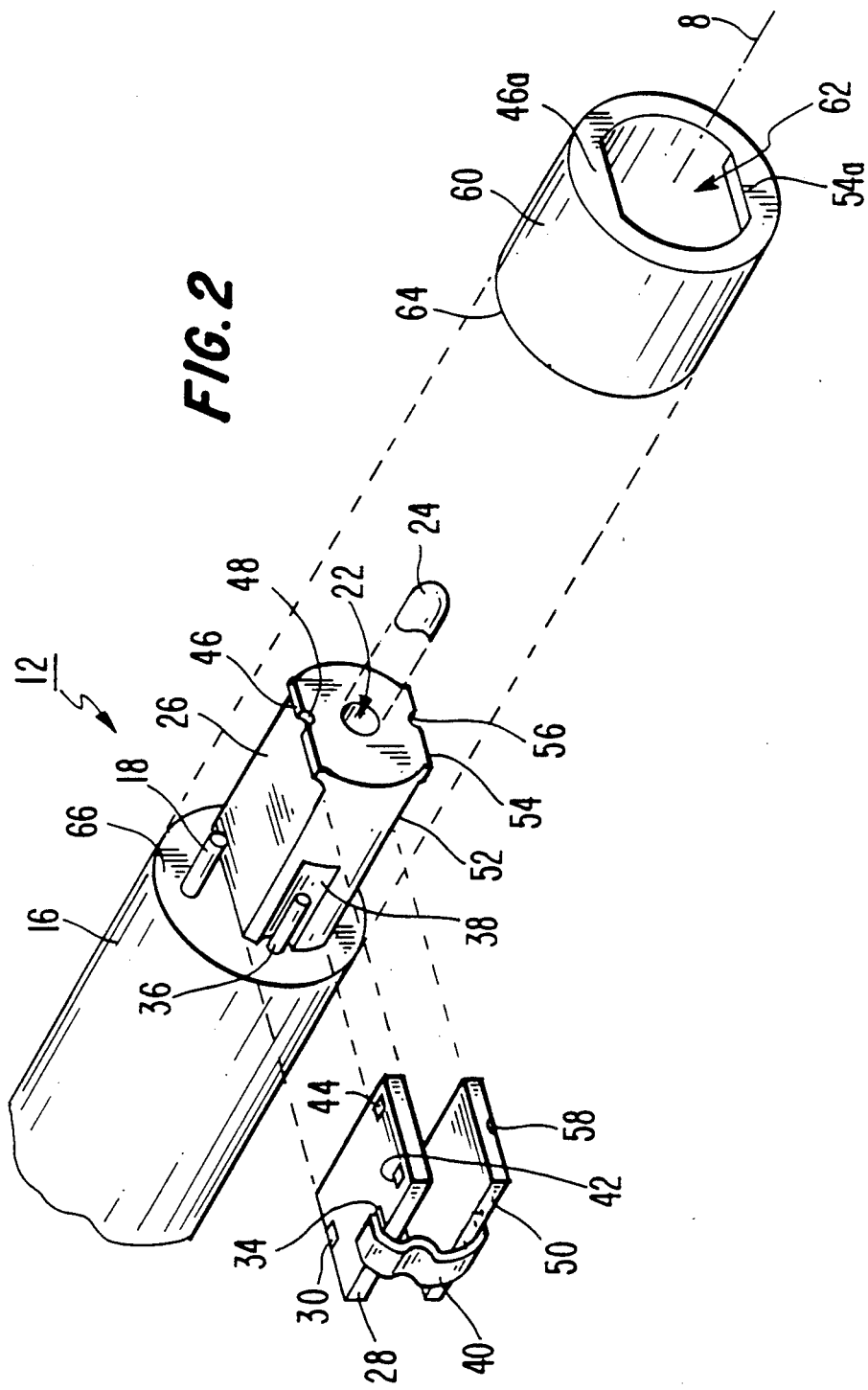

CATHETER WITH DISTALLY LOCATED INTEGRATED CIRCUIT RADIATION GENERATOR

BACKGROUND OF THE INVENTION

This invention relates to angioplasty using radiation is generated by one or more integrated circuits located at the distal end of the catheter.

Many people die suddenly in the United States each year from acute myocardial infarction, and many more suffer from chronic heart problems. A major contributing factor in both acute and chronic heart problems is a reduction in the flow of nutrient blood to the muscles of the heart, resulting from a reduction of blood flow through coronary blood vessels. The reduction in flow may be caused by deposits of atherosclerotic plaque on the walls of the blood vessel, which causes a narrowing of the lumen or channel of the blood vessel. When the lumen is sufficiently narrowed, the rate of flow of blood may be so diminished that spontaneous formation of a thrombus or clot occurs by a variety of physiological mechanisms. As is known, once a blood clot has started to develop, it extends within minutes into the surrounding blood, in part because the proteolytic action of thrombin acts on prothrombin normally present, tending to split this into additional thrombin which causes additional clotting. Thus, the presence of atherosclerotic plaque not only reduces the blood flow to the heart muscle which it nourishes, but is a major predisposing factor in coronary thrombosis.

Among the treatments available for the conditions resulting from plaque formations are pharmacological means such as the use of drugs, for example nitroglycerin, for dilating the coronary blood vessels to improve flow. In those cases too far advanced to be manageable by drugs, surgical treatment may be indicated. One of the surgical techniques commonly used is the coronary bypass, in which the substitute blood vessel shunts or bypasses blood around the blockage. The bypass operation is effective but is expensive and subject to substantial risks.

Percutaneous transluminal balloon catheter angioplasty is an alternative form of treatment. This method involves insertion of a deflated balloon into the lumen of an artery partially obstructed by plaque, and inflation of the balloon in order to enlarge the lumen. The lumen remains expanded after removal of the catheter. The major problem with this technique is restenosis of the narrowed vessel by recurrence of the arterial plaque.

Another technique which has recently received a great deal of attention is transluminal laser catheter angioplasty. This treatment involves introduction into the coronary artery of a fiber optic cable, the proximal end of which is connected to a laser energy source. The distal end of the fiber optic cable is directed towards the plaque. The laser is pulsed, and the resulting high energy light traverses the fiber optic cable and exits from the distal end thereof to penetrate or vaporize a portion of the plaque. Many problems remain unsolved in laser catheter angioplasty. Among the problems are the difficulty in matching the characteristics of available lasers with the characteristics of fiber optic cables. In particular, the wavelengths at which fiber optic cables having mechanical properties suiTABLE for use in catheters carry light energy with low losses do not necessarily correspond to the wavelengths at which lasers radiate the maximum energy. Consequently, a substantial amount of light energy produced by a laser may not be transmitted or may be absorbed by the fiber optic cable extending throughout the length of the catheter. Furthermore, the connectors by which light is coupled from a laser source to the proximal end of the fiber optic cable of the catheter may introduce attenuation. Thus, the exact amount of light energy or power arriving at the distal end of the fiber optic cable extending through the catheter may not be known.

Microwave aided balloon angioplasty is described in U.S. Pat. No. 4,643,186 issued Feb. 7, 1987 in the name of Rosen et al. In the arrangement as described by Rosen et al., a catheter including a microwave transmission line terminates at its distal end in an antenna. The antenna is surrounded by a balloon. During angioplasty, the catheter is introduced into a blood vessel or other vas, and the distal end with the balloon and the antenna is manipulated to a point adjacent the plaque. Microwave power is applied to the proximal end of the catheter and flows to the antenna, which radiates electromagnetic energy. The electromagnetic energy penetrates the soft tissue and the plaque for heating and thereby softening the plaque. The balloon is expanded against the softened plaque to thereby expand the lumen of the blood vessel. It should be noted that there is no difference in kind between the light radiated by the laser and the microwave power which is radiated by an antenna, both being oscillatory electromagnetic radiation, with different frequencies of oscillation.

A microwave transmission line of the coaxial type which is described in the aforementioned Rosen et al. arrangement may advantageously have certain ratios of the diameters of the center and outer conductors in order to transmit energy most effectively. As is known to those skilled in the art, for maximum power the characteristic impedance of a coaxial transmission line must be in the vicinity of 50 ohms, whereas for lowest loss the characteristic impedance should be near 70 ohms. The very small size of the cable tends to result in relatively large losses. These losses may be so great that up to half the microwave power applied to the proximal end of the transmission line may not reach the distal end for application to the tissue. Instead, this power is dissipated in the form of heat, which tends to be greatest at the proximal end. Since the heat is concentrated within the relatively small transmission line rather than being distributed throughout a larger volume of flesh, the transmission line may become hot enough to cause burns at the point at which the catheter enters the body. Furthermore, the cross-sectional shape of the microwave transmission line makes it difficult to add other functions such as fiber optic scopes and the like. In particular, since the center conductor of a coaxial transmission line is desirably in the center of the cross-section, and surrounded by a cylindrical insulator of known dielectric constant, it is difficult to arrange an axial aperture in the catheter for a guide wire or filament. An improved catheter is desired.

SUMMARY OF THE INVENTION

A catheter includes at least one semiconductor radiation emitter adapted for electromagnetic radiation when electrically energized. An elongated electrical insulator includes proximal and distal ends adapted to be introduced into a vas. First and second elongated electrical conductors are electrically isolated by the insulator. The distal ends of the electrical conductors are connected to the semiconductor, so that electrical energy coupled to the proximal ends of the conductors energizes the semiconductor to cause radiation. In a particular embodiment of the invention, the semiconductor radiation emitter is a laser. In another embodiment, it is an oscillator. In yet another embodiment, two semiconductor radiator emitters are located distally on the catheter, and each is connected to one of the electrical conductors. According to one aspect of the invention, a third conductor may be connected in common to both semiconductor radiation emitters. The catheter may include an antenna to aid in coupling radiation from a semiconductor radiation emitter to the surrounding tissue. The catheter may also include an axial aperture adapted for use with a guide filament. A balloon may be connected to the distal end of the catheter, and be coupled by a fluid aperture to the proximal end for filling and emptying.

DESCRIPTION OF THE DRAWING

FIG. 1a is a longitudinal cross-section of a catheter according to the invention, FIG. 1b is an end view of the proximal portion, and FIG. 1c is a cross-sectional end view of the distal region taken along the section lines c—c, with certain portions removed FIGS. 1a,1b and 1c are together referred to as FIG. 1;

FIG. 2 is a perspective or isometric view, from one side, of the distal region of the catheter of FIG. 1, with certain portions removed and other portions exploded;

DESCRIPTION OF THE INVENTION

Figure 3:
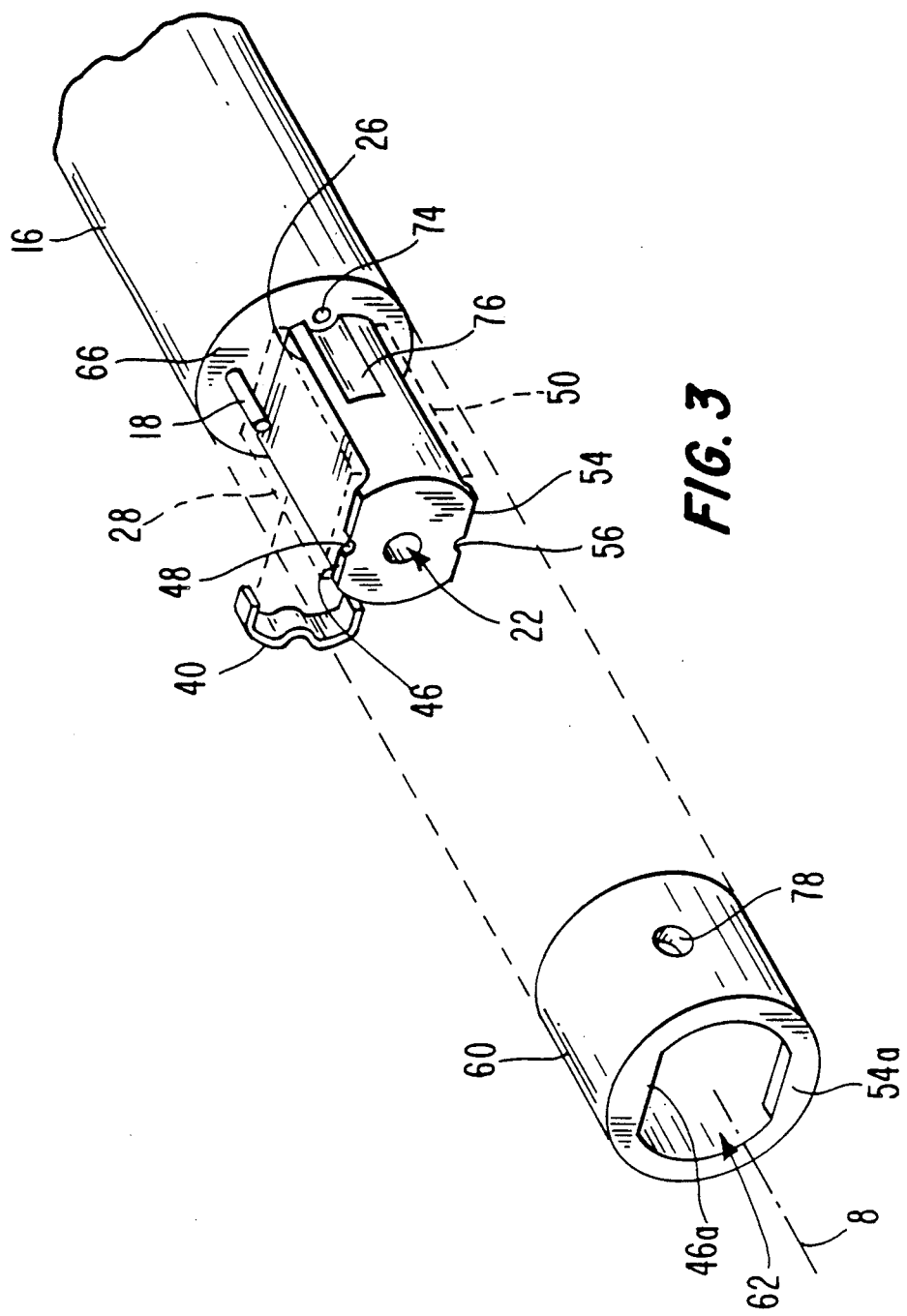
FIG. 3 is a view similar to FIG. 2, from the other side.

FIG. 1 illustrates a catheter according to the invention. In FIG. 1a, a catheter designated generally as 10 includes a distal end 12 and a proximal end 14. An elongated cylindrical electrical insulator 16 extends from distal end 12 to proximal end 14. First and second electrical conductors 18 and 20, respectively, extend from a region near the distal end 12 to the proximal end 14. Electrical conductors 18 and 20 are electrically isolated from each other by insulator 16. This may be accomplished in well-known fashion by extrusion of insulating material 16 in liquid form around conductors 18 and 20. Insulator 16 and its associated structures are flexible so that catheter 10 may follow the curves of a blood vessel or other vas.

Insulator 16 also defines an circular axial aperture 22 which extends all the way through the insulator from the distal and proximal ends and which has a circular cross-section. Aperture 22 is dimensioned for a sliding fit with a guide wire or filament illustrated as 24.

Figure 4A:
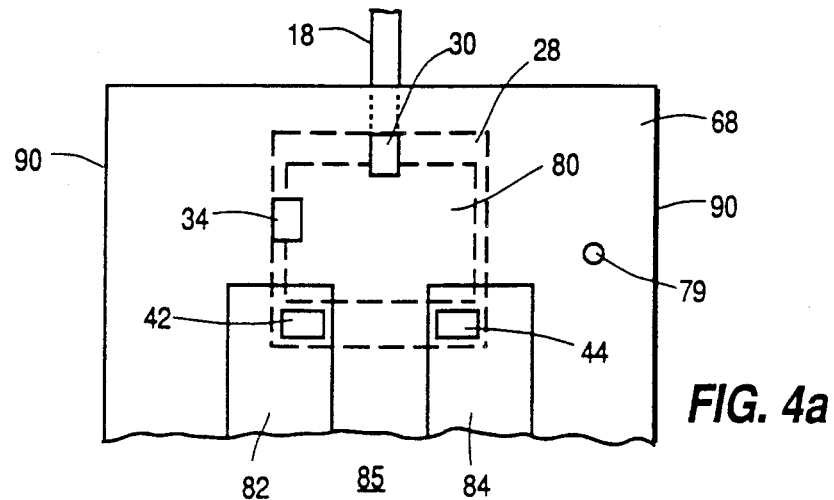
FIG. 4a is a plan view of a semiconductor radiation emitter, illustrating its relationship to a conductor pattern formed near a neck region of a balloon, which neck region is illustrated in developed form.

At the distal end of catheter 10, electrical insulator 16 is cut away or formed to define a flat region 26 illustrated in perspective or isometric view in FIGS. 2 and 3. Elements of FIGS. 2 and 3 corresponding to those of FIG. 1 are designated by the same reference numerals. Flat region 26 is dimensioned to fit and support a first semiconductor chip or integrated circuit illustrated as 28. For this purpose, surface 26 is spaced away from the exposed end of conductor 18 by the thickness of the semiconductor chip. When assembled, chip 28 is fastened to surface 26 in an appropriate fashion, as by the use of adhesives. The exposed end of conductor 18 may be electrically connected to an electrode illustrated as 30 which is defined on semiconductor chip 28 and is illustrated in FIGS. 2 and 4a. A suitable electrical connection may be made by the use of solder. A solder fillet is illustrated as 32 is FIG. 1c. Electrode 30 is one of two electrodes of chip 28 which together are adapted for receiving electrical energy, normally in the form of an applied voltage.

Integrated circuit or chip 28 is a generator of electromagnetic radiation. Those skilled in the art know that such electromagnetic radiation may be at various frequencies and that it may cover a band of frequencies. Within a first band of frequencies, the electromagnetic radiation may be in the form of light, and at other, lower frequencies, may be in the form of invisible radiation which is commonly known as microwave radiation. Such microwave radiation is useful for heating plaque, as described in detail in the aforementioned Rosen et al. patent.

Semiconductor chip 28 includes a second electrode 34 adapted for coacting with electrode 30 for being connected for receiving electrical energy. An electrical conductor 36 extends from distal end 14 of catheter 10 to the region of distal end 12, at which end it is exposed by a notch 38 cut into insulator 16, best seen in FIG. 2. A thin metallic spring clip 40 bears against the upper surface of chip 28 at electrode 34 and against the side of conductor 36 for helping to hold semiconductor chip 28 in place and for providing an electrical connection between upper electrode 34 and conductor 36. Spring clip 40 may be soldered in place when assembly is complete, if desired.

As so far described, integrated circuit 28 is arranged to receive electrical power applied to the proximal ends of conductors 18 and 36, which are in electrical communication with electrodes 30 and 34. When energized, integrated circuit 28 generates electromagnetic radiation. If semiconductor chip 28 includes an oscillator and/or an amplifier for generating microwave oscillations, electromagnetic radiation will occur. At many frequencies of oscillation, it may be desirable to provide an antenna to enhance the radiation by improving the coupling between the circuits formed on the semiconductor chip and the surrounding tissues. At some frequencies, the antenna may be formed as an integral part of semiconductor chip 28. At other frequencies, it may be desirable to couple the oscillations to a separate antenna. For this purpose chip 28 may include electrodes illustrated as 42 and 44 in FIGS. 2 and 4a. The separate antenna is described below in conjunction with the discussion of FIG. 4.

Distally of flat surface 26, insulator 16 defines a retaining lip 46. A notch 48 formed in lip 46 allows emission of a light beam from chip 28 if chip 28 is a laser for generation of electromagnetic radiation at light frequencies. If chip 28 is a laser, the antenna or radiating aperture is formed as part of the integrated circuit.

It may be desirable to provide only microwave heating of the tissues in the region of the distal end of catheter 10, or to project laser energy. For some purposes, however, it may be desirable to have the ability to generate both laser energy and microwave energy. For this purpose, a second semiconductor chip 50 is mounted on another flat 52 formed on insulator 16. Flat 52 defines a further lower retaining lip 54 and a further notch 56. When chip 50 is assembled onto flat 52, an electrode may be soldered to wire 20 as illustrated by solder fillet 58 in FIG. 1c, and another electrode (not illustrated) may be contacted by clip 40. Thus, semiconductor chip 50 may be electrically energized by way of conductors 20 and 36, as described below. When so assembled, a lasing region 58 of chip 50 may be aligned with notch 56 so that a beam of light may be projected along a path parallel to axis 8.

As illustrated in FIGS. 1, 2 and 3, a sleeve 60 of electrically insulating material such as, for example, tetrafluoroethane (Teflon) has an outer diameter substantially equal to the outer diameter of cylindrical insulator 16 and defines a bore 62 dimensioned to fit over chips 28 and 50, clip 40, and wires 18, 20 and 36. Sleeve 60 prevents contact of body fluids with any portion of the circuitry within sleeve 60, as described further below. The proximal end 64 of sleeve 60 makes a fluid-tight connection to a flat face 66 of insulator 16. An adhesive or welded bond may be formed between proximal end 64 of sleeve 60 and flat face 66 of insulator 16. At the extreme distal end of insulator 16, lips 46 and 54 make a fluid-tight seal against flats 46a and 54a, respectively, defined by the inner bore of sleeve 60. Notches 46 and 48 may be sealed with a clear elastomer.

If balloon angioplasty is to be performed, a balloon membrane illustrated as 68 in FIG. 1a may be provided. Balloon membrane 68 includes a first mouth or os 70 which surrounds and makes a fluid-tight seal to the exterior of insulator 16 in a region 72. At the distal end of balloon membrane 68, a second os surrounds lips 46 and 48, and other regions of insulator 16, and is pressed into a tight fit by sleeve 60. Suitable adhesives may be used to improve the sealing. The balloon defined by membrane 68 may be inflated and deflated by a fluid channel illustrated as 74 in FIGS. 1b, 1c and 3. Communication between fluid channels 74 and the interior of the balloon defined by membrane 68 is provided by a channel or notch 76 formed in the side of insulator 16, as illustrated in particular in FIG. 3, and by a corresponding aperture 78 in the side of sleeve 60. During assembly, that portion of the balloon lying directly between aperture 78 of sleeve 60 and notch 76 in insulator 16 may be punctured with a small sharp instrument to guarantee a path of the fluid flow.

FIG. 4a illustrates how connections are made between electrodes 42 and 44 of a microwave energy generator on chip 28. Elements of FIG. 4 corresponding to those of FIGS. 1, 2 or 3 are designated by corresponding reference numerals. In FIG. 4a, a portion of membrane 68 is illustrated, developed from cylindrical to flat form. In FIG. 4a, the balloon membrane 68 is illustrated as being split along a line 90 which is at the bottom of the balloon in FIG. 1. Balloon membrane 68 in FIG. 4a overlies integrated circuit chip 28. The region of chip 28 in which circuits are located is illustrated by a dotted-line portion 80. The circuits are well known and are not illustrated in detail. The circuits are connected to electrodes 42 and 44. Electrodes 42 and 44 are overlaid by the ends of conductors 82 and 84, respectively, of a transmission line designated generally as 85. If conductors 82 and 84 are printed on the upper surface of balloon membrane 68 as illustrated in FIG. 4a, through vias (conductive through paths) must be formed through membrane 68 at locations above electrodes 42 and 44 to make the connection through the membrane. If conductors 82 and 84 are formed on the lower surface of membrane 68 as viewed in FIG. 4a, a direct connection may be made. Such a direct connection may be made by placing a droplet of a conductive elastomer on each of electrodes 42 and 44, followed by a placement of the balloon membrane. The elasticity of the balloon membrane will hold the balloon in place while the conductive elastomer dries to make the electrical contact, and placement of sleeve 60 (FIGS. 1, 2 or 3) will thereafter guarantee continued contact. Also visible in FIG. 4a is an aperture 79 formed in balloon membrane 68. Aperture 69 corresponds to the location of aperture 78 in sleeve 60, as illustrated in FIG. 3, and provides a path for the flow of fluid between the interior of the balloon and fluid channel 74.

Figure 4B:
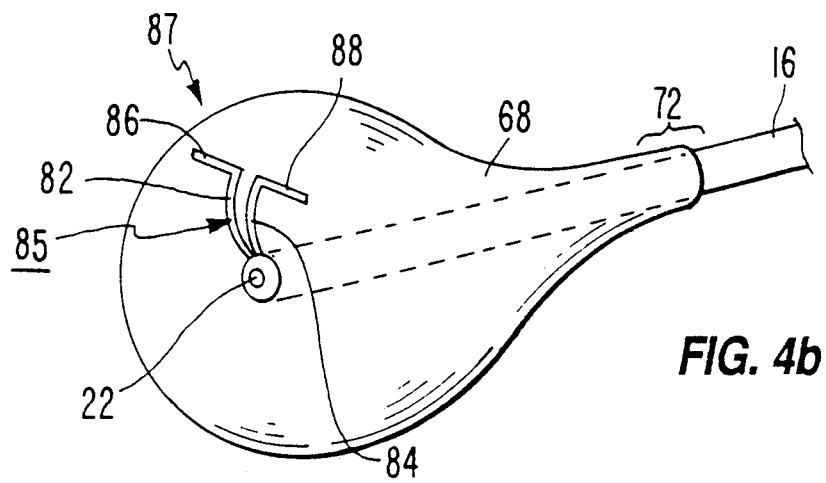
FIG. 4b is a perspective or isometric view of a portion of the catheter of FIG. 1 with the balloon inflated.

FIG. 4b illustrates balloon membrane 68 in its inflated form, with conductors 82 and 84 formed thereon to define a transmission line 85 which extends to an antenna. As illustrated in FIG. 4b, antenna 87 is a dipole including a first dipole half 86 connected to the end of transmission-line conductor 82, and a second dipole half 88 is connected to the end of transmission-line conductor 84. Naturally, other types of antennas may be used. Antenna 87 may be either on an interior or exterior of balloon membrane 68. If exterior, the conductive paths should be made from physiologically inert materials.

Figure 5:
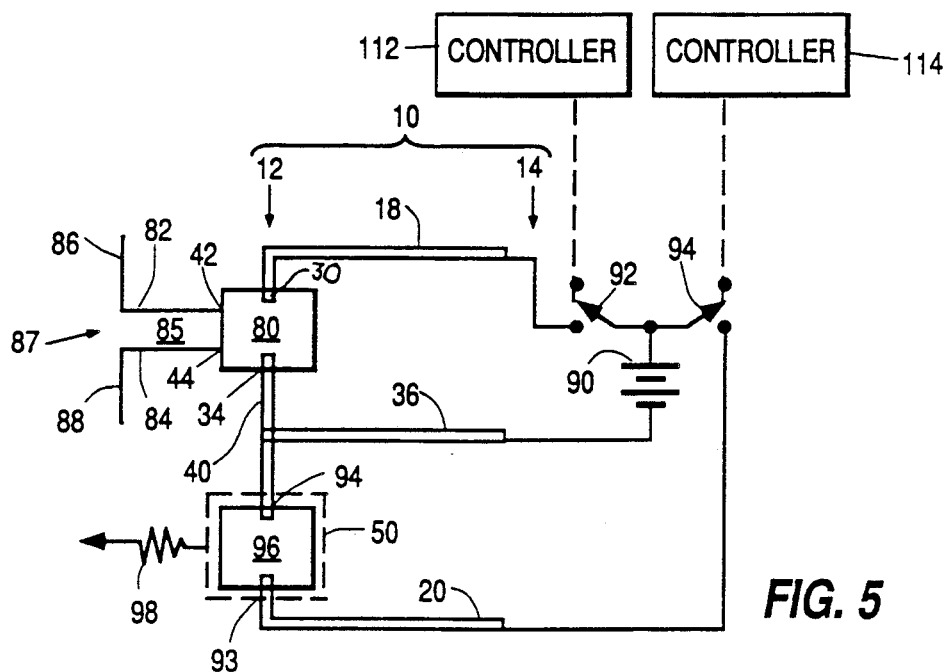
FIG. 5 is a schematic diagram illustrating electrical connections which may be made to the catheter to energize either or both semiconductor radiation emitters.

FIG. 5 is a schematic diagram illustrating electrical connections which allow the various radiation generators to be energized. Elements of FIG. 5 corresponding to those of FIG. 4 are designated by the same reference numerals. In FIG. 5, the circuits designated generally as 80 on chip 28 at the distal end of catheter 10 are illustrated as being connected by conductors 18 and 20, 36, respectively to proximal end 14. A source of direct voltage illustrated as a battery 90 has its positive terminal connected by a switch 92 to the proximal end of conductor 18. The negative side of battery 90 is connected to the proximal end of conductor 36. The positive end of battery 90 is also connected by way of a switch 94 to the proximal end of conductor 20. Conductor 20 at distal end 12 is connected to laser circuitry designated generally as 96 formed on integrated circuit 50.

As so far described, switches 92 and 94 may be manually operated. In addition, switches 92 and 94 may be controlled portions of relays, controlled by pulse-width controllers illustrated as 112 and 114. Duty cycle control for power regulation is well known and needs no further explanation. Naturally, the controllers may be independent or linked. While switches 92 and 94 are illustrated as mechanical, their solid-state equivalents are preferred.

In operation, catheter 10 is inserted into a vas and positioned with its distal end 12 adjacent a region to be subjected to electromagnetic radiation treatment. For treatment with electromagnetic energy at the frequency produced by circuits 80 of integrated circuit or chip 28, switch 92 of FIG. 5 is closed to apply voltage from battery 90 for energization of circuits 80, whereby electromagnetic energy is generated by circuits 80 and applied over transmission line 85 for radiation by antenna 87. In conjunction therewith or separately therefrom, switch 94 may be closed to apply the voltage of battery 90 to laser 96, for causing light radiation illustrated in FIG. 5 by photon symbol 98. The voltage may be applied to either or both of the chips for a predetermined time or until a desired effect is achieved, and may be applied during inflation of balloon membrane 68.

Other embodiments of the invention will be apparent to those skilled in the art. In particular, central or axial aperture 22 (FIGS. 1, 2) may include arrangements for limiting the ingress of blood (in the case of catheterization of a blood vessel) or of other bodily fluids (in the case of catheterization of a vas other than a blood vessel) when guide wire 24 is retracted. While only two electromagnetic radiation generators have been described, additional generators may be spaced about axis 8 on flats defined at the distal end of insulator 16. As an alternative to or in addition to the radial arrangement of semiconductor integrated circuits about axis 8, a fore-and-after configuration is possible, with the most proximal of the radiation generators coupled for radiation by transmission lines which extend past the more proximal semiconductor integrated circuits to more distally-placed antennas. The catheter may include other known elements in addition to those described, such as fiber-optic scopes for viewing the region being treated, "hot" wires which may be heated by the laser or by the electromagnetic radiation from the oscillator for performing cutting, additional fluid channels for applying medication or aspirating fluid or debris, and the like. While a source of direct voltage has been illustrated for energization of the integrated circuits, alternating voltage may be used if the chips include rectifiers for rectifying the resulting current, in which case, it should be noted, the only difference between the electrical energy applied to the proximal end of the catheter and the electrical energy radiated into the flesh lies in the frequency, and it is apparent that the integrated circuits are nothing more than frequency converters.

What is claimed is:

1. A catheter, comprising:
   a semiconductor oscillator including first and second electrodes adapted for the application of energizing voltage thereto for generating electromagnetic radiation in response to application of said energizing voltage;
   an elongated electrically insulating piece defining proximal and distal ends, said distal end being adapted to be introduced into a vas;
   first and second elongated electrical conductive means electrically isolated by at least said elongated electrically insulating piece, said first and second elongated electrically conductive means each defining proximal and distal ends;
   first electrical connecting means coupled to said first electrode of said semiconductor oscillator and to said distal end of said first elongated conductive means for providing electrical continuity therebetween;
   second electrical connecting means coupled to said second electrode of said semiconductor radiation emitter and to said distal end of said second elongated conductive means for providing electrical continuity therebetween; and
   mechanical connecting means coupled to said oscillator and to said electrically insulating piece for mechanical coupling thereof to form an assemblage which is adapted to be introduced into a vas.

2. A catheter according to claim 1 wherein said proximal ends of said first and second conductive means are adapted to be coupled to the terminals of a source of direct voltage.

3. A catheter according to claim 1 wherein said proximal ends of said first and second conductive means are adapted to be coupled to the terminals of a source of pulsed direct voltage.

4. A catheter according to claim 1 wherein said semiconductor oscillator comprises a laser.

5. A catheter according to claim 1 further comprising means for enhancing the transition from said oscillator to regions exterior of said catheter.

6. A catheter according to claim 5 wherein said means for enhancing comprises an antenna.

7. A catheter according to claim 1 wherein said elongated electrically insulating piece defines an axial aperture.

8. A catheter according to claim 7 further comprising a guide filament extending at least part-way through said axial aperture.

9. A catheter, comprising:
   a semiconductor radiation emitter including first and second electrodes adapted for the application of energizing voltage thereto;
   an elongated electrically insulating piece defining proximal and distal ends, said distal end being adapted to be introduced into a vas;
   first and second elongated electrical conductive means electrically isolated by at least said elongated electrically insulating piece, said first and second elongated electrically conductive means each defining proximal and distal ends;
   first connecting means coupled to said first electrode of said semiconductor radiation emitter and to said distal end of said first elongated conductive means for providing electrical continuity therebetween; and
   second connecting means coupled to said second electrode of said semiconductor radiation emitter and to said distal end of said second elongated conductive means for providing electrical continuity therebetween;
   and further comprising a second semiconductor radiation emitter, including first and second electrodes for the application of energizing voltage thereto.

10. A catheter according to claim 9 further comprising third connecting means for electrically connecting radiation emitter to said distal end of said first elongated conductive means.

11. A catheter according to claim 10 further comprising:
    a third elongated electrically conductive means electrically independent of said first and second elongated electrically conductive means, said third elongated electrically conductive means defining proximal and distal ends; and
    fourth connecting means coupled to said distal end of said third elongated electrically conductive means and to said second electrode of said second semiconductor radiation emitter for providing electrical continuity therebetween.

12. A catheter according to claim 11 wherein said first semiconductor radiation emitter comprises a laser for radiating electromagnetic energy in the form of light defining a frequency and said second semiconductor radiation emitter comprises an electrical oscillator for radiating electromagnetic energy having a natural frequency below that of the light radiated by said laser.

13. A catheter according to claim 12 further comprising an antenna located adjacent said distal end of said insulating piece and electrically coupled to said electrical oscillator for directing radiation at the frequency of said electrical oscillator.

14. A method for performing angioplasty, comprising the steps of:
   introducing into a vas the distal end of a cable including elongated mutually electrically insulated multiple electrical conductors, near the distal end of which is located an oscillator adapted for, when electrically energized, producing electromagnetic radiation at least somewhat capable of penetrating through flesh;
   positioning said distal end of said cable adjacent a region to which electromagnetic radiation is to be applied;
   applying direct electrical power across at least two of said electrical conductors to thereby energize said oscillator for causing said radiation; and
   ceasing said applying step after a predetermined time.

15. A catheter, comprising:
   first and second elongated, mutually electrically insulated electrical conductors defining proximal and distal ends, said proximal ends being adapted for being coupled to a source of electrical power defining a first frequency, which frequency may include zero frequency; and
   frequency conversion means connected near said distal end of said first and second conductors and, together with said conductors, being dimensioned and arranged for introduction of at least said distal end into a vas, for generating electromagnetic radiation at a frequency different from said first frequency, and for coupling said electromagnetic radiation to surrounding tissue.

16. A catheter according to claim 15 further comprising means for preventing body fluids from coming into contact with said frequency conversion means.

* * * * *